US012642689B2

(12) United States Patent
Gloeckner et al.

(10) Patent No.: US 12,642,689 B2
(45) Date of Patent: Jun. 2, 2026

(54) FEMALE EXTERNAL CATHETERS AND METHODS THEREOF

(71) Applicant: C. R. Bard, Inc., Franklin Lakes, NJ (US)

(72) Inventors: D. Claire Gloeckner, Lilburn, GA (US); Matthew J. Rothberg, Atlanta, GA (US); Seth C. Schneider, Social Circle, GA (US); Jonathan Robichaud, Decatur, GA (US); Michael Bailey, Creedmoor, NC (US); James David Hughett, Sr., Monroe, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 190 days.

(21) Appl. No.: 18/284,046

(22) PCT Filed: Mar. 30, 2022

(86) PCT No.: PCT/US2022/022669
§ 371 (c)(1),
(2) Date: Sep. 25, 2023

(87) PCT Pub. No.: WO2022/216507
PCT Pub. Date: Oct. 13, 2022

(65) Prior Publication Data
US 2024/0164937 A1 May 23, 2024

Related U.S. Application Data

(60) Provisional application No. 63/173,220, filed on Apr. 9, 2021.

(51) Int. Cl.
*A61F 5/455* (2006.01)
*A61F 5/44* (2006.01)
*A61F 5/441* (2006.01)

(52) U.S. Cl.
CPC ............ *A61F 5/455* (2013.01); *A61F 5/4401* (2013.01); *A61F 5/4408* (2013.01); *A61F 5/441* (2013.01)

(58) Field of Classification Search
CPC ...... A61F 5/451; A61F 5/4401; A61F 5/4408; A61F 5/443
See application file for complete search history.

(56) References Cited

U.S. PATENT DOCUMENTS 1,113,561 A    10/1914   Jorgenson
1,241,652 A    10/1917   Norquist
(Continued)

FOREIGN PATENT DOCUMENTS

CN    106510930 A    3/2017
CN    212369143 U    1/2021
(Continued)

OTHER PUBLICATIONS

Dictionary.com. (Sep. 9, 2017). Spheroid definition meaning. Dictionary. com. https://www.dictionary.com/browse/ spheroid (Year: 2017).
(Continued)

*Primary Examiner* — Guy K Townsend
(74) *Attorney, Agent, or Firm* — Rutan & Tucker LLP

(57) ABSTRACT

Disclosed herein are female external catheters ("FECs") and methods thereof. For example, an FEC can include a catheter body, a catheter back, and a connector. The catheter body can include a cavity extending along a length of the catheter body. The cavity is configured to open toward a patient. The catheter back can include a connector hole aligned with an end portion of the cavity. The connector hole can be configured to open away from the patient. The connector is disposed in the connector hole. The connector can include a sump configured to collect urine from the end portion of the cavity for withdrawal from the FEC. In
(Continued)

another example, a method of an FEC can includes a method of using the FEC.

24 Claims, 11 Drawing Sheets

(56)                References Cited

U.S. PATENT DOCUMENTS

| | | | | | |
|---|---|---|---|---|---|
| 3,512,185 | A | | 5/1970 | Ellis | |
| 4,106,490 | A | | 8/1978 | Spilman et al. | |
| 4,202,058 | A | | 5/1980 | Anderson | |
| 4,305,161 | A | | 12/1981 | Diaz | |
| 4,756,029 | A | | 7/1988 | Zieve et al. | |
| 4,784,654 | A | | 11/1988 | Beecher | |
| 5,002,541 | A | | 3/1991 | Conkling et al. | |
| 5,091,998 | A | | 3/1992 | Witzke | |
| 5,895,349 | A | | 4/1999 | Tihon | |
| 6,332,878 | B1 | | 12/2001 | Wray et al. | |
| 6,428,521 | B1 | | 8/2002 | Droll | |
| 7,181,781 | B1 | | 2/2007 | Trabold et al. | |
| 8,287,508 | B1 | * | 10/2012 | Sanchez | A61F 5/4404 604/326 |
| 8,663,181 | B2 | | 3/2014 | Yang | |
| 8,690,847 | B2 | | 4/2014 | Norman | |
| 8,795,248 | B2 | | 8/2014 | Shihata | |
| 10,226,376 | B2 | * | 3/2019 | Sanchez | A61F 5/443 |
| 10,390,989 | B2 | * | 8/2019 | Sanchez | A61D 99/00 |
| D898,190 | S | | 10/2020 | Cohn et al. | |
| 10,857,025 | B2 | * | 12/2020 | Davis | A61F 5/451 |
| 10,898,367 | B2 | | 1/2021 | Nelson | |
| 10,952,889 | B2 | * | 3/2021 | Newton | A61F 5/4404 |
| 10,973,678 | B2 | * | 4/2021 | Newton | A61M 1/88 |
| 11,026,829 | B2 | * | 6/2021 | Harvie | A61M 25/0017 |
| D928,946 | S | * | 8/2021 | Sanchez | D24/122 |
| 11,376,152 | B2 | * | 7/2022 | Sanchez | A61D 99/00 |
| 11,382,786 | B2 | * | 7/2022 | Sanchez | A61F 5/4404 |
| 11,426,303 | B2 | * | 8/2022 | Davis | A61F 5/4408 |
| 11,529,252 | B2 | * | 12/2022 | Glithero | A61F 5/455 |
| 2003/0195483 | A1 | | 10/2003 | Ching | |
| 2006/0149195 | A1 | | 7/2006 | Oprandi | |
| 2008/0287894 | A1 | * | 11/2008 | Van Den Heuvel | A61F 5/455 604/327 |
| 2009/0182296 | A1 | | 7/2009 | Dennis et al. | |
| 2009/0204092 | A1 | | 8/2009 | Loyd et al. | |
| 2009/0254040 | A1 | | 10/2009 | Bierman et al. | |
| 2011/0040271 | A1 | | 2/2011 | Rogers | |
| 2011/0054426 | A1 | | 3/2011 | Stewart | |
| 2012/0103347 | A1 | | 5/2012 | Wheaton et al. | |
| 2013/0218112 | A1 | * | 8/2013 | Thompson | A61F 5/455 604/347 |
| 2015/0135423 | A1 | | 5/2015 | Sharpe et al. | |
| 2015/0366699 | A1 | | 12/2015 | Nelson | |
| 2016/0317698 | A1 | | 11/2016 | Berryman et al. | |
| 2016/0367226 | A1 | * | 12/2016 | Newton | A01K 23/005 |
| 2016/0374848 | A1 | * | 12/2016 | Sanchez | A61F 5/455 604/319 |
| 2017/0007438 | A1 | * | 1/2017 | Harvie | A61F 5/453 |
| 2017/0035600 | A1 | | 2/2017 | Preciado | |
| 2017/0266031 | A1 | * | 9/2017 | Sanchez | A61F 5/443 |
| 2017/0348139 | A1 | * | 12/2017 | Newton | A61F 5/4404 |
| 2018/0228642 | A1 | * | 8/2018 | Davis | A61B 5/208 |
| 2019/0038451 | A1 | * | 2/2019 | Harvie | A61F 5/441 |
| 2019/0142624 | A1 | * | 5/2019 | Sanchez | A61F 5/453 604/319 |
| 2019/0224036 | A1 | * | 7/2019 | Sanchez | A61F 5/455 |
| 2019/0314190 | A1 | * | 10/2019 | Sanchez | A61F 5/443 |
| 2020/0046544 | A1 | * | 2/2020 | Godinez | A61F 5/455 |
| 2020/0138620 | A1 | | 5/2020 | Schwab | |
| 2020/0390591 | A1 | * | 12/2020 | Glithero | A61F 5/4401 |
| 2021/0059853 | A1 | * | 3/2021 | Davis | A61B 5/208 |
| 2021/0069005 | A1 | * | 3/2021 | Sanchez | A61F 5/4404 |
| 2021/0069008 | A1 | * | 3/2021 | Blabas | A61F 5/455 |
| 2021/0220162 | A1 | * | 7/2021 | Jamison | A61F 5/453 |
| 2021/0228795 | A1 | * | 7/2021 | Hughett | A61F 5/451 |
| 2021/0236323 | A1 | * | 8/2021 | Austermann | A61F 5/451 |
| 2021/0275343 | A1 | * | 9/2021 | Sanchez | A61F 5/4404 |
| 2021/0353450 | A1 | * | 11/2021 | Sharma | A61F 5/4408 |
| 2021/0369495 | A1 | * | 12/2021 | Cheng | A61F 5/451 |
| 2022/0031290 | A1 | | 2/2022 | Weed | |
| 2022/0062029 | A1 | * | 3/2022 | Johannes | A61F 5/4401 |
| 2022/0071811 | A1 | * | 3/2022 | Cheng | A61F 5/4404 |
| 2022/0117774 | A1 | * | 4/2022 | Meyer | A61F 5/455 |
| 2022/0117775 | A1 | * | 4/2022 | Jones | A61L 26/0009 |
| 2022/0133524 | A1 | * | 5/2022 | Davis | A61M 1/60 604/319 |
| 2022/0151817 | A1 | * | 5/2022 | Mann | A61F 5/451 |
| 2022/0152352 | A1 | | 5/2022 | Hughett, Sr. | |
| 2022/0257407 | A1 | * | 8/2022 | Johannes | A61F 5/453 |
| 2022/0265462 | A1 | * | 8/2022 | Alder | A61F 5/4404 |
| 2022/0280357 | A1 | * | 9/2022 | Jagannathan | A61F 13/84 |
| 2022/0313222 | A1 | * | 10/2022 | Austermann | A61F 5/455 |
| 2022/0354685 | A1 | * | 11/2022 | Davis | A61B 5/208 |
| 2022/0370234 | A1 | * | 11/2022 | Hughett | A61F 5/4405 |
| 2022/0387001 | A1 | * | 12/2022 | Askenazi | A61F 5/455 |
| 2022/0395391 | A1 | * | 12/2022 | Saunders | A61F 5/4404 |
| 2023/0023781 | A1 | | 1/2023 | Watson | |
| 2023/0089032 | A1 | * | 3/2023 | Hughett | A61F 5/4401 604/319 |
| 2023/0138269 | A1 | * | 5/2023 | Abdelal | A61F 5/451 604/347 |
| 2023/0277362 | A1 | * | 9/2023 | Davis | A61B 5/208 604/319 |
| 2024/0299205 | A1 | | 9/2024 | Hughett, Sr. | |
| 2025/0367020 | A1 | | 12/2025 | Robichaud et al. | |

FOREIGN PATENT DOCUMENTS

| | | | | | |
|---|---|---|---|---|---|
| GB | 1422638 | A | * | 1/1976 | A61G 9/006 |
| KR | 101901532 | B1 | | 9/2018 | |
| WO | 2002000148 | A2 | | 1/2002 | |
| WO | 2007050716 | A1 | | 5/2007 | |
| WO | 2019206941 | A1 | | 10/2019 | |
| WO | 2021211729 | A1 | | 10/2021 | |
| WO | 2022216507 | A1 | | 10/2022 | |
| WO | 2023244238 | A1 | | 12/2023 | |

OTHER PUBLICATIONS

U.S. Appl. No. 17/528,037, filed Nov. 16, 2021 Final Office Action dated Feb. 15, 2024.

U.S. Appl. No. 17/528,037, filed Nov. 16, 2021 Non-Final Office Action dated Nov. 8, 2023.

U.S. Appl. No. 17/850,444, filed Jun. 27, 2022 Advisory Action dated Jan. 18, 2024.

U.S. Appl. No. 17/850,444, filed Jun. 27, 2022 Final Office Action dated Jul. 17, 2024.

U.S. Appl. No. 17/850,444, filed Jun. 27, 2022 Final Office Action dated Oct. 26, 2023.

U.S. Appl. No. 17/850,444, filed Jun. 27, 2022 Non-Final Office Action dated Feb. 7, 2024.

PCT/US2022/022669 filed Mar. 30, 2022 International Search Report and Written Opinion dated Jul. 15, 2022.

PCT/US2022/033886 filed Jun. 16, 2022 International Search Report and Written Opinion dated Jan. 19, 2023.

U.S. Appl. No. 17/528,037, filed Nov. 16, 2021 Advisory Action dated Sep. 22, 2023.

U.S. Appl. No. 17/528,037, filed Nov. 16, 2021 Final Office Action dated Jul. 10, 2023.

U.S. Appl. No. 17/528,037, filed Nov. 16, 2021 Non-Final Office Action dated Jan. 24, 2023.

U.S. Appl. No. 17/850,444, filed Jun. 27, 2022 Non-Final Office Action dated Jun. 22, 2023.

U.S. Appl. No. 17/850,444, filed Jun. 27, 2022 Advisory Action dated Sep. 19, 2024.

U.S. Appl. No. 17/850,444, filed Jun. 27, 2022 Non-Final Office Action dated Jan. 31, 2025.

U.S. Appl. No. 18/664,024, filed May 14, 2024 Non-Final Office Action dated Dec. 13, 2024.

(56)            References Cited

OTHER PUBLICATIONS

Wolfram Mathworld Spherical Sector "https://web.archive.org/web/
20180715224119/https://mathworld.wolfram.com/SphericalSector.
html" Jul. 15, 2018 (Year: 2018).
U.S. Appl. No. 17/850,444, filed Jun. 27, 2022 Notice of Allowance
dated Jul. 25, 2025.
U.S. Appl. No. 18/664,024, filed May 14, 2024 Final Office Action
dated Jul. 15, 2025.

* cited by examiner

FEMALE EXTERNAL CATHETERS AND METHODS THEREOF

PRIORITY

This application is a U.S. national stage application of International Application No. PCT/US2022/022669, filed Mar. 30, 2022, which claims the benefit of priority to U.S. Provisional Application No. 63/173,220, filed Apr. 9, 2021, each of which is incorporated by reference in its entirety into this application.

BACKGROUND

Female external catheters ("FECs") are indicated for non-invasive urine-output management in incontinent female patients. Generally, such catheters operate by drawing urine from the patients into urine-drainage systems. Because the FECs are to be worn for up to 8 or more hours at a time, efficiency in drawing the urine away from the patients is important for reducing moisture buildup and, in turn, development of dermatitis. In addition, comfort can be an issue for certain patients while wearing the FECs for the 8-or-more hours at a time. As such, there is an ongoing need to improve both the efficiency of FECs in drawing urine away from patients and the comfort of the FECs. Disclosed herein are FECs and methods thereof that address at least the foregoing.

SUMMARY

Disclosed herein is an FEC including, in some embodiments, a catheter body, a catheter back, and a connector. The catheter body includes a cavity extending along a length of the catheter body. The cavity is configured to open toward a patient. The catheter back includes a connector hole aligned with an end portion of the cavity. The connector hole is configured to open away from the patient. The connector is disposed in the connector hole. The connector includes a sump configured to collect urine from the end portion of the cavity for withdrawal from the FEC.

In some embodiments, the catheter body and the catheter back are integral.

In some embodiments, the FEC further includes a stabilizer extending from the catheter back. The stabilizer is configured for stabilizing the FEC on the patient using an intergluteal cleft of the patient.

In some embodiments, the stabilizer is integral with the catheter back.

In some embodiments, the catheter back includes a tubing channel. The tubing channel extends along a length of the catheter back from the connector hole through an end of the catheter back opposite the connector hole.

In some embodiments, the FEC further includes catheter tubing disposed in the tubing channel. The catheter tubing includes an end portion disposed in the connector.

In some embodiments, the connector includes a pair of wings extending from a connector back. The pair of wings is disposed in a pair of recesses of the catheter back such that the catheter back and the connector back are flush.

In some embodiments, the catheter body and the catheter back are formed of an open-cell foam.

In some embodiments, the open-cell foam has a durometer and bulk modulus sufficient to provide comfort to the patient for up to 8 or more hours.

In some embodiments, the FEC further includes an impermeable cavity coating over a surface of the cavity. The cavity coating is configured to prevent the urine from passing into the open-cell foam of the catheter body or the catheter back.

In some embodiments, the FEC further includes an open-cell foam insert disposed in the cavity. The insert is configured to allow the urine to pass therethrough for collection by the sump.

In some embodiments, the insert has a durometer and bulk modulus sufficient to provide comfort to the patient for up to 8 or more hours without compressing to an extent that prevents the urine form passing through the insert.

In some embodiments, the FEC further includes one or more intake layers disposed over the insert.

In some embodiments, the catheter body and the catheter back are two thermoformed pieces of the FEC.

In some embodiments, the FEC further includes a removable stabilizer extending from the catheter back. The stabilizer is configured for stabilizing the FEC on the patient using an intergluteal cleft of the patient.

In some embodiments, the FEC further includes catheter tubing including an end portion disposed in the connector.

In some embodiments, the FEC further includes an open-cell foam insert disposed in the cavity. The insert is configured to allow the urine to pass therethrough for collection by the sump.

In some embodiments, the insert has a durometer and bulk modulus sufficient to provide comfort to the patient for up to 8 or more hours without compressing to an extent that prevents the urine form passing through the insert.

In some embodiments, the catheter body includes a positioning knoll over the end portion of the cavity. The positioning knoll is configured to be aligned with a vaginal introitus when the FEC is tucked between inner labia.

In some embodiments, the FEC further includes a vent between the catheter body and the catheter back. The vent passes through a cavity bottom of the cavity and the catheter back in another end portion of the FEC opposite that including the connector hole.

In some embodiments, the catheter back includes a depression along a length of the catheter back. The depression is configured to facilitate pinching and folding the FEC lengthwise for positioning the FEC to collect the urine.

In some embodiments, the catheter back includes a pair of side notches evenly distributed in a pair of major sides of the back. The pair of side notches are configured to facilitate pinching and folding the FEC lengthwise for positioning the FEC to collect the urine.

In some embodiments, the pair of side notches are contoured with contoured finger surfaces.

In some embodiments, the contoured finger surfaces are textured with ridges, bumps, or dimples.

Also disclosed herein is a method of an FEC. The method includes, in some embodiments, a connecting step, a disposing step, a switching step, and a urinating step. The connecting step includes connecting catheter tubing of the FEC to urine-drainage tubing of a remainder of a urine-drainage system including the FEC. The disposing step includes disposing an open-cell foam insert of the FEC over a urethral opening. The insert is disposed in a cavity of the FEC, which cavity includes a sump in an end portion of the cavity. The switching step includes switching on a pump of a pump unit of the urine-drainage system to draw a vacuum through the insert. The urinating step includes urinating into the FEC such that urine is drawn through the insert, into the sump, and out the catheter tubing to the urine-drainage tubing.

In some embodiments, the method further includes a stabilizing step. The stabilizing step includes disposing a stabilizer of the FEC in an intergluteal cleft. The stabilizer extends from a back of the FEC in an opposite direction than the catheter tubing.

In some embodiments, the method further includes another switching step, an exchanging step, and a repeating step. The other switching step includes switching off the pump to stop drawing the vacuum. The exchanging step includes exchanging the FEC for a fresh FEC every 8 to 12 hours or as needed. The repeating step includes repeating the connecting step, the disposing step, the switching step, and the urinating step with the fresh FEC.

These and other features of the concepts provided herein will become more apparent to those of skill in the art in view of the accompanying drawings and following description, which describe particular embodiments of such concepts in greater detail.

DRAWINGS

Figure 2:
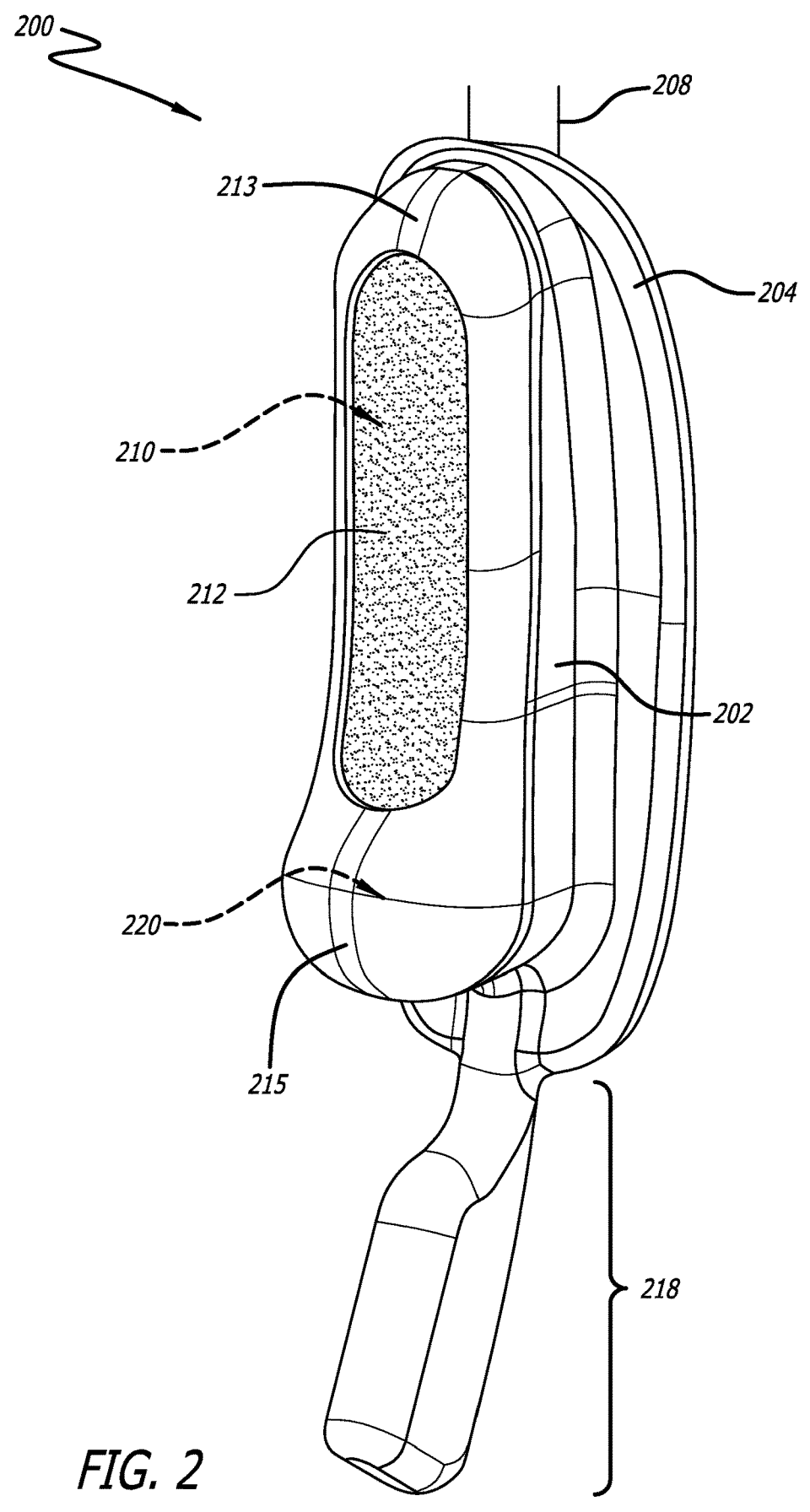

FIG. 2 illustrates a first view of a first FEC in accordance with some embodiments.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

Unless defined otherwise, all technical and scientific terms used herein have the same meaning as commonly understood by those of ordinary skill in the art.

As set forth above, there is an ongoing need to improve both the efficiency of FECs in drawing urine away from patients and the comfort of the FECs. Disclosed herein are FECs and methods thereof that address at least the foregoing.

Systems

Figure 1:
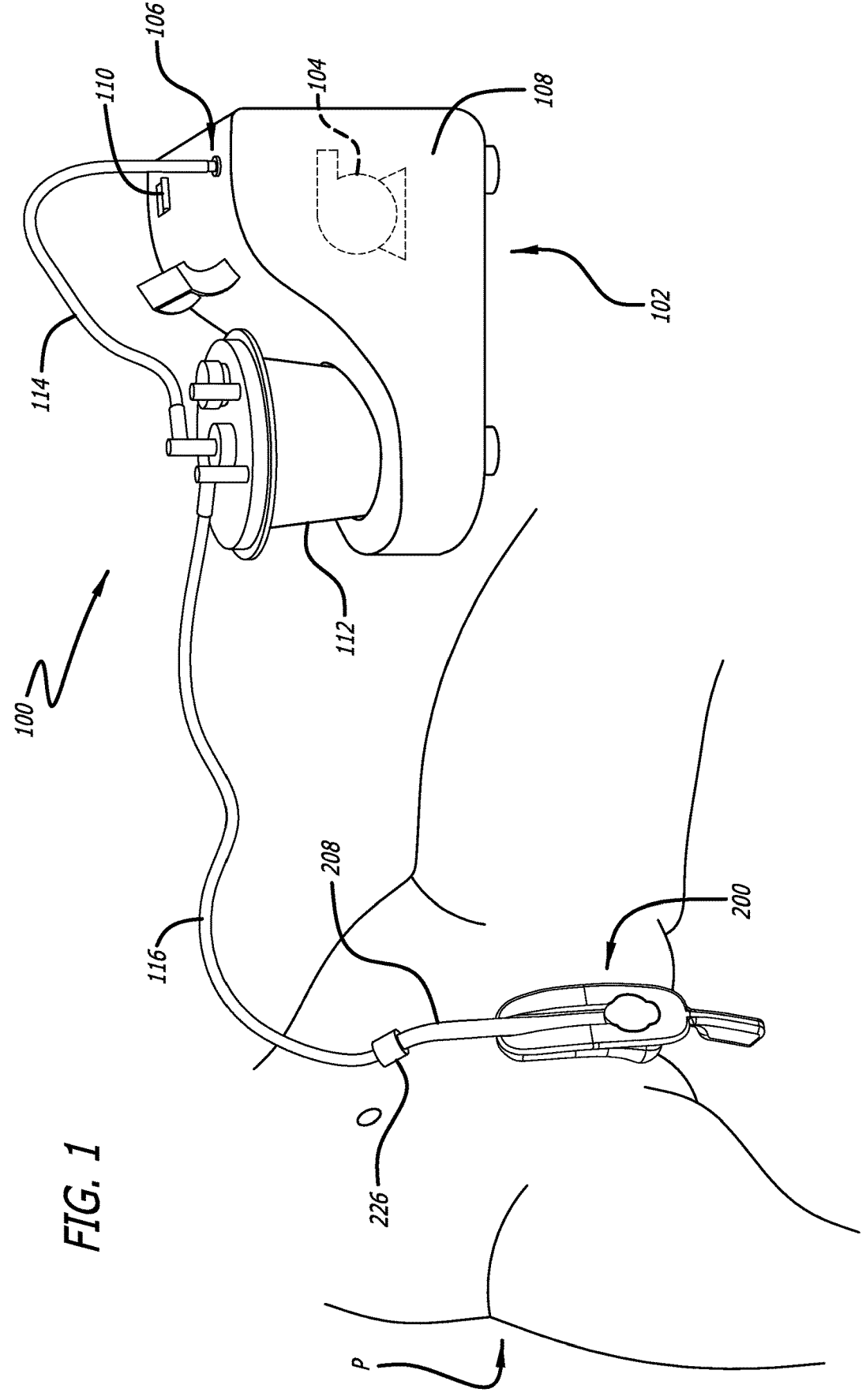
FIG. 1 illustrates a urine-drainage system including an FEC in accordance with some embodiments.

FIG. 1 illustrates a urine-drainage system 100 including the FEC 200 in accordance with some embodiments.

As shown, the urine-drainage system 100 can include a pump unit 102 and the FEC 200 or any other FEC like that set forth herein. Notably, the pump unit 102 and its associated equipment (e.g., the collection canister 112, the urine-drainage tubing 116) is multi-use equipment and the FEC 200 or any other FEC like that set forth herein is single-use equipment; however, use of some of the multi-use equipment associated with the pump unit 102 can be more limited than that of the pump unit 102 itself as such multi-use equipment might need to be periodically replaced.

The pump unit 102 includes an internal pump 104. The pump 104 is configured to draw a vacuum through an inlet 106 in a housing 108 of the pump unit 102 when a toggle switch 110 is switched on. The pump 104 is also configured to stop drawing a vacuum through the inlet 106 when the toggle switch 110 is switched off. While not shown, the pump unit 102 can be powered by a general-purpose alternating-current (AC) electric power supply or one or more batteries.

The multi-use equipment associated with the pump unit 102 can include a urine-collection canister 112, pump tubing 114, and urine-drainage tubing 116. The pump tubing 114 is configured to fluidly connect the pump 104 to the urine-collection canister 112. The urine-drainage tubing 116 is configured to fluidly connect the urine-collection canister 112 to the FEC 200 or any other FEC like that set forth herein. When such multi-use equipment is fluidly connected to the FEC 200 or any other FEC like that set forth herein, urine can be drawn from the FEC, through the urine-drainage tubing 116, and into the urine-collection canister 112 when the toggle switch 110 is switched on.

Female External Catheters

Figures 3, 4:
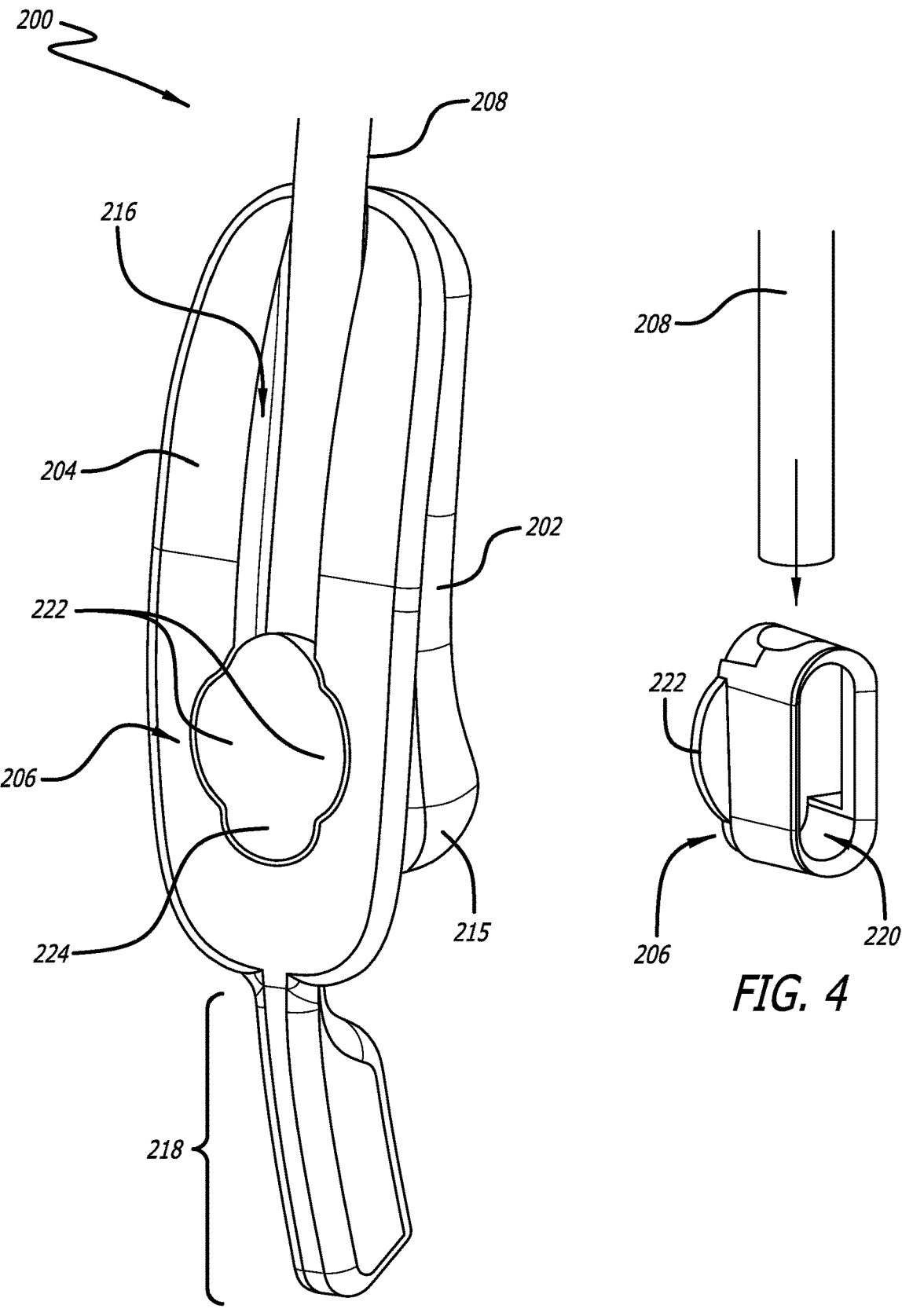
FIG. 3 illustrates a second view of the first FEC in accordance with some embodiments.
FIG. 4 illustrates a connector of at least the first FEC in accordance with some embodiments.
Figure 5:
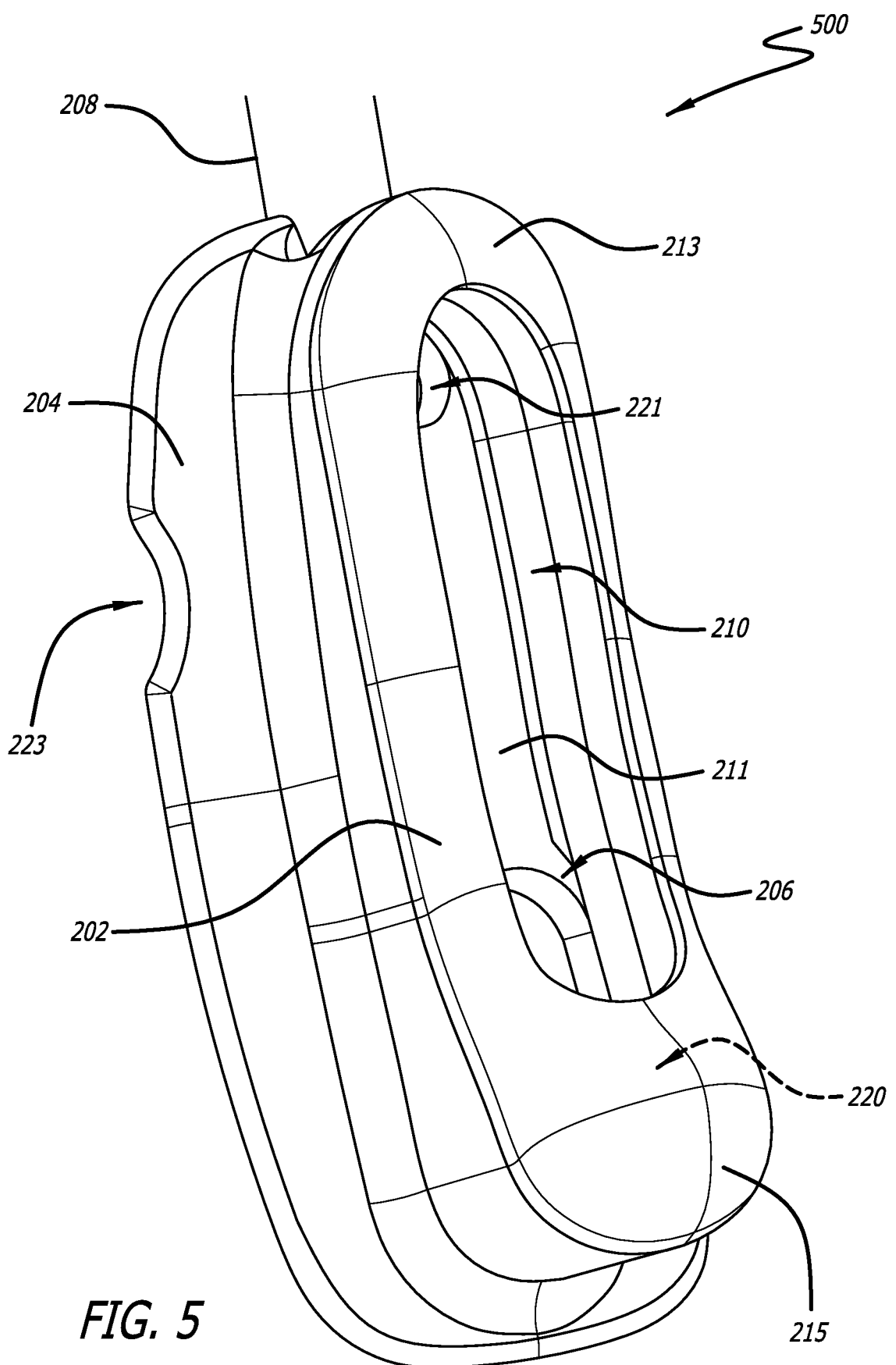
FIG. 5 illustrates a view of a second FEC in accordance with some embodiments.
Figure 7:
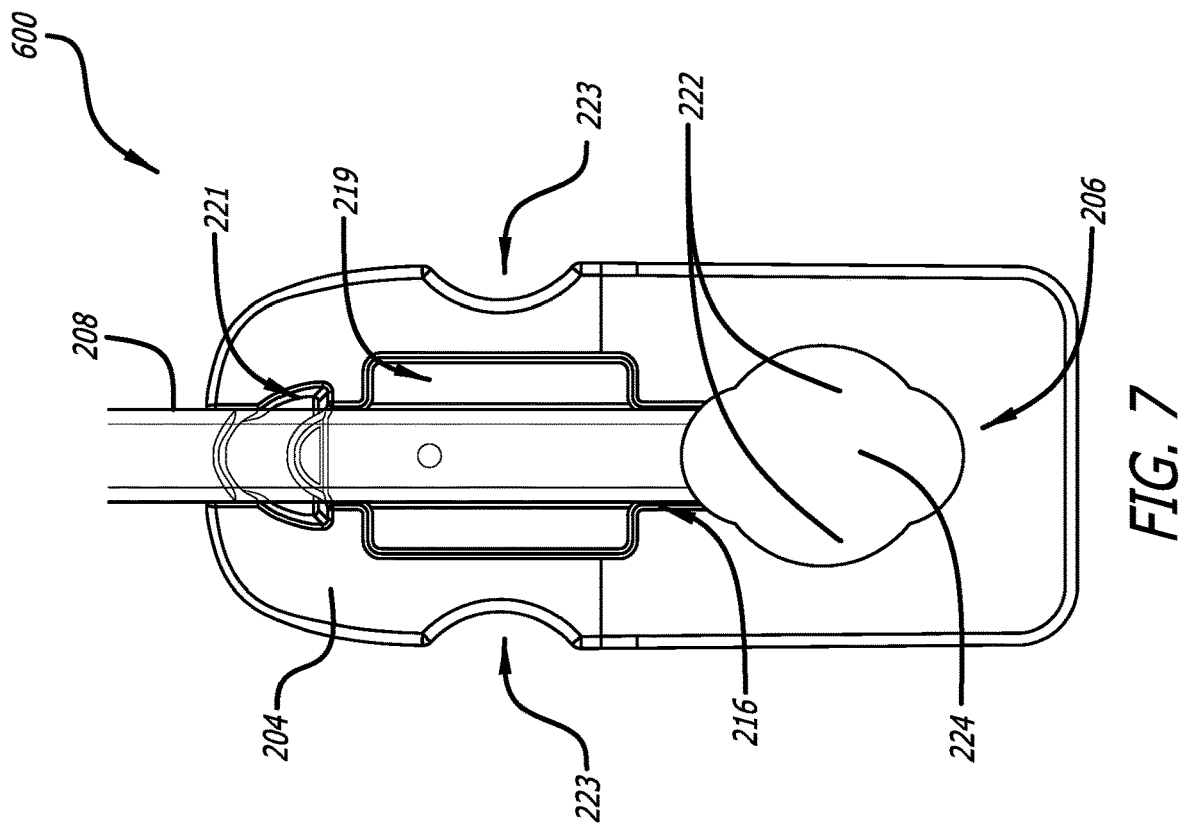
FIG. 7 illustrates a second view of the third FEC in accordance with some embodiments.
Figure 6:
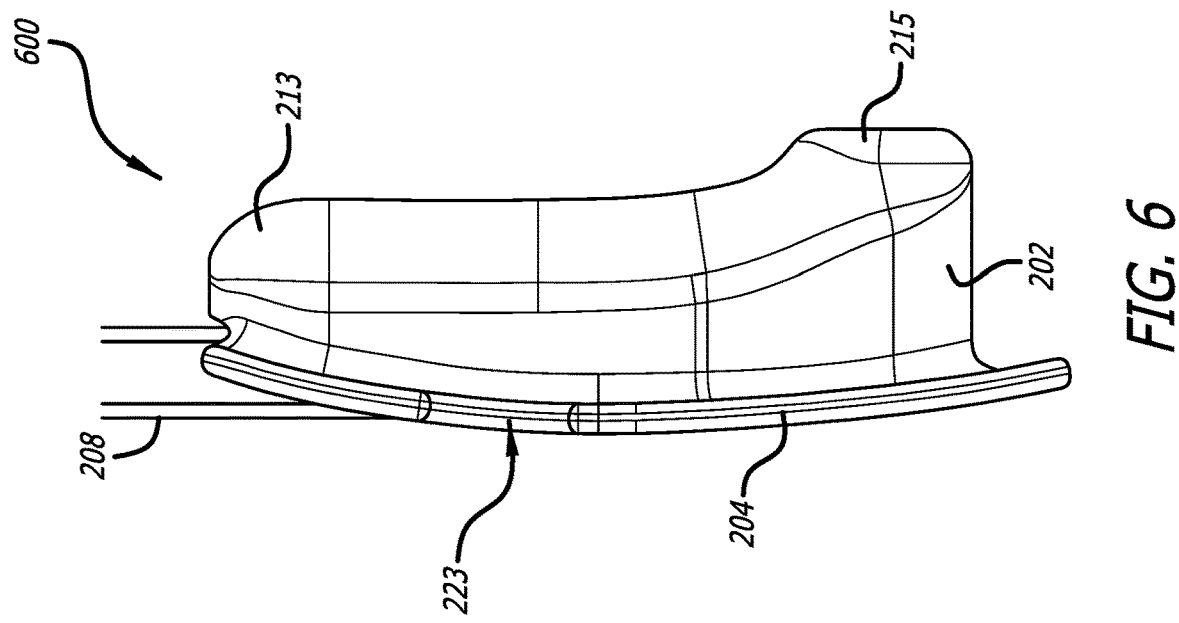
FIG. 6 illustrates a first view of a third FEC in accordance with some embodiments.
Figure 8:
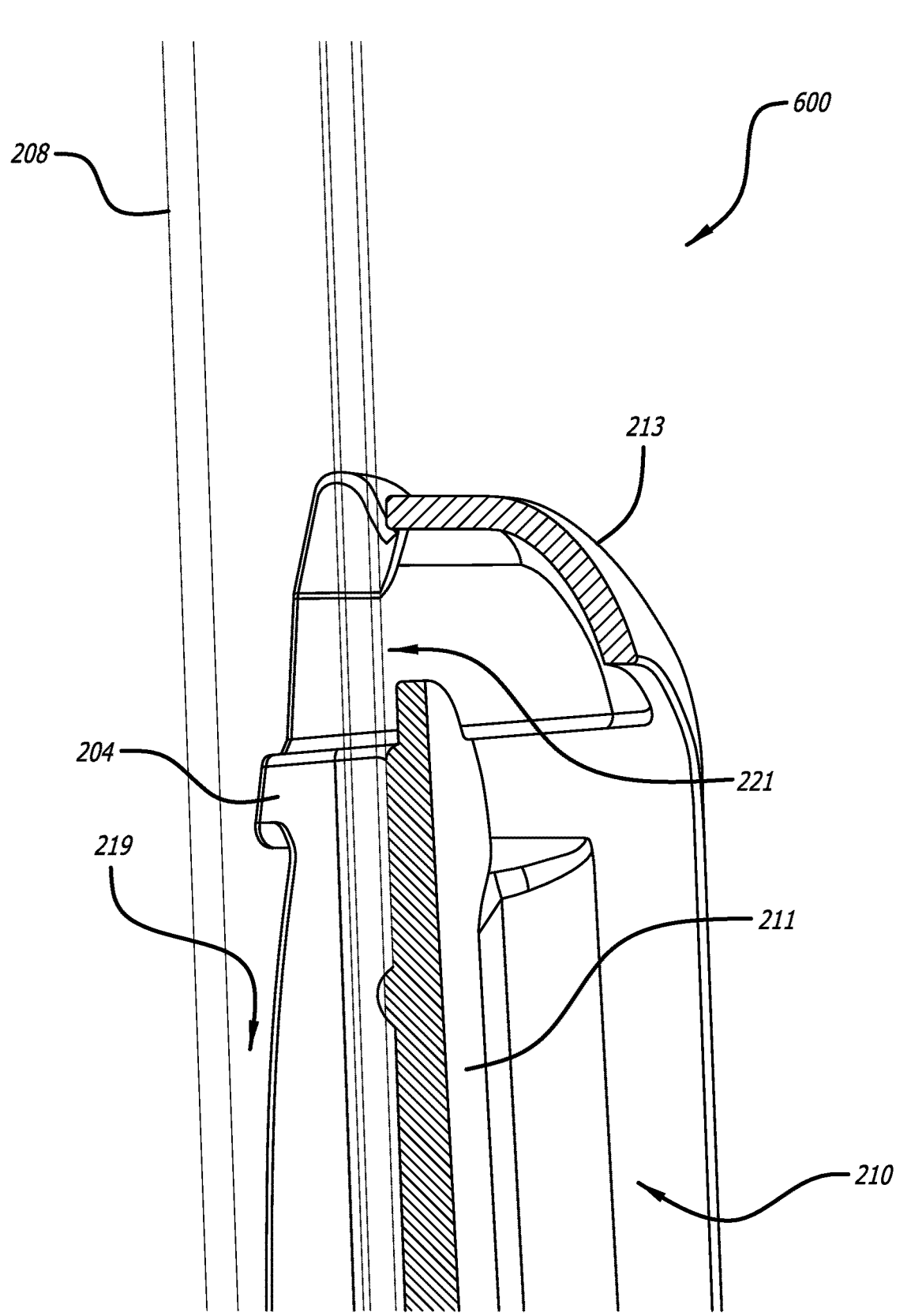
FIG. 8 illustrates a third view of the third FEC in accordance with some embodiments.
Figure 10:
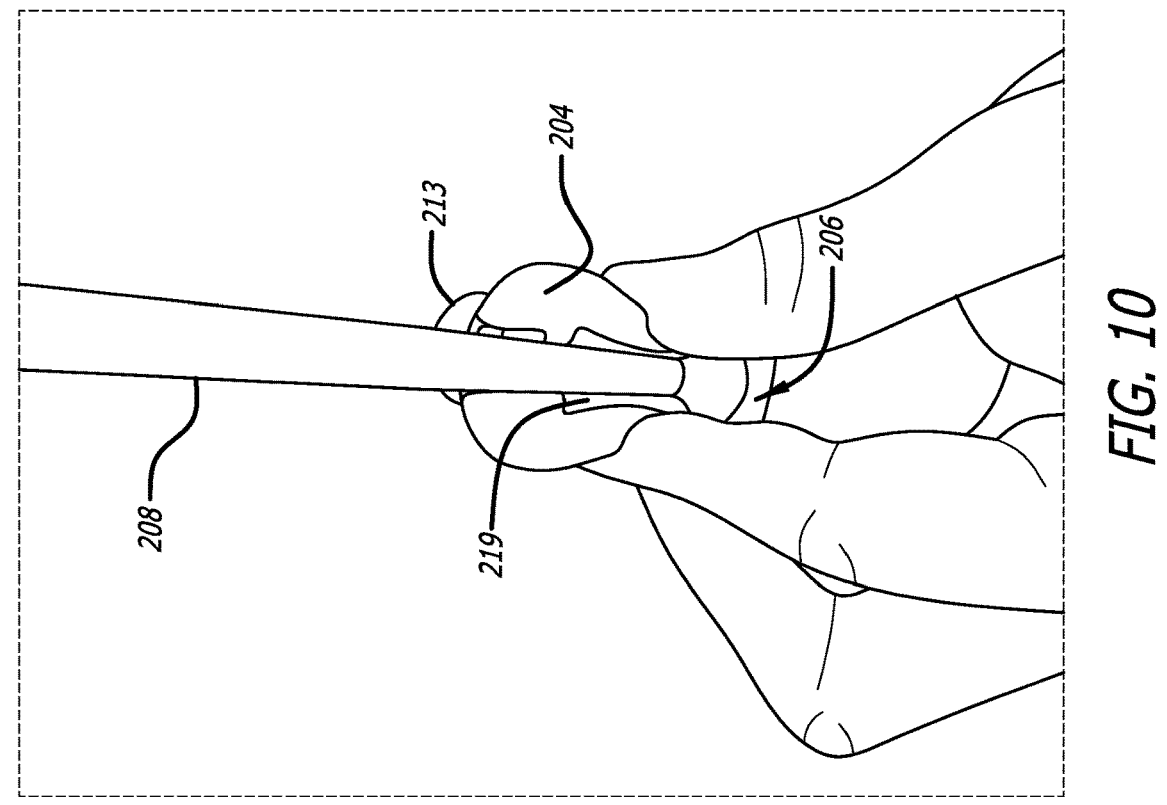
FIG. 10 illustrates the third FEC while being gripped for positioning in accordance with some embodiments.
Figure 9:
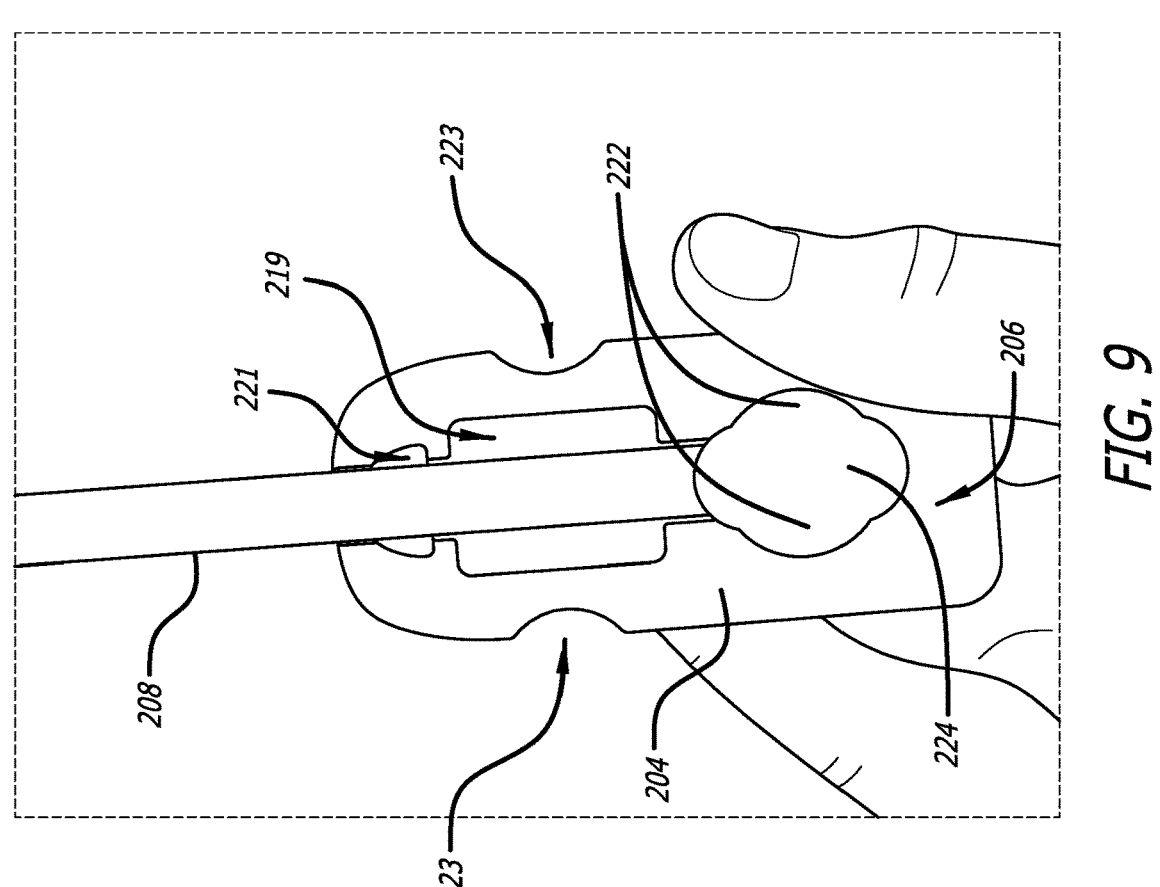
FIG. 9 illustrates the third FEC before being gripped for positioning in accordance with some embodiments.
Figure 13:
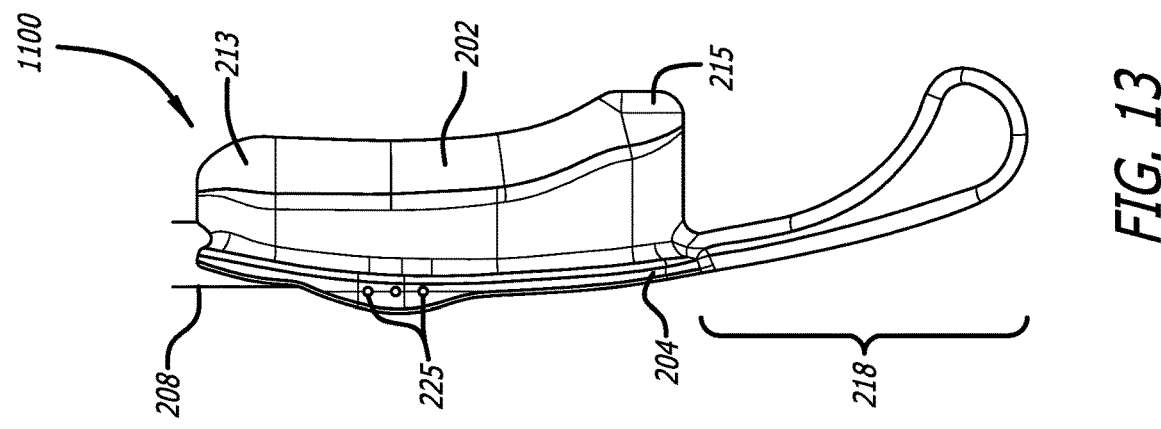
FIG. 13 illustrates a third view of the fourth FEC with an intergluteal cleft in accordance with some embodiments.
Figure 12:
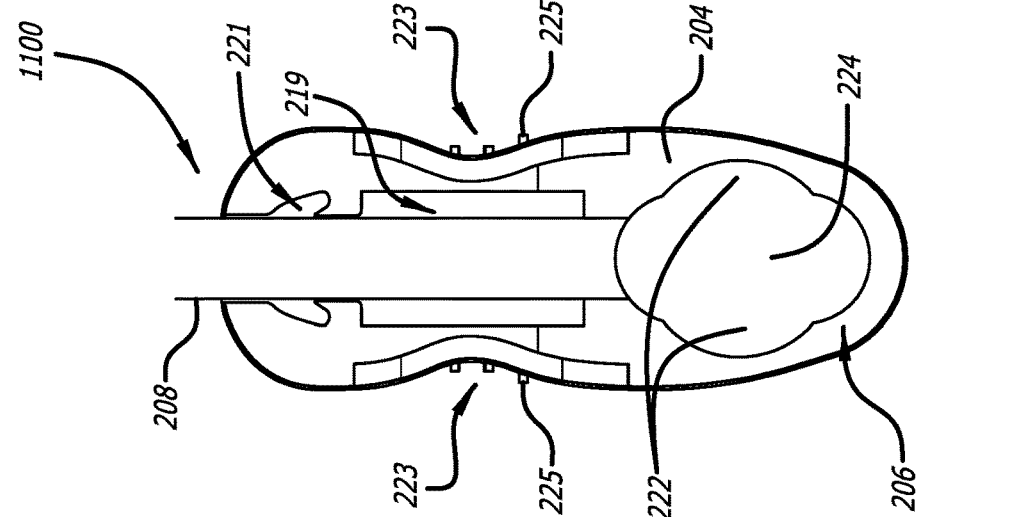
FIG. 12 illustrates a second view of the fourth FEC in accordance with some embodiments.
Figure 11:
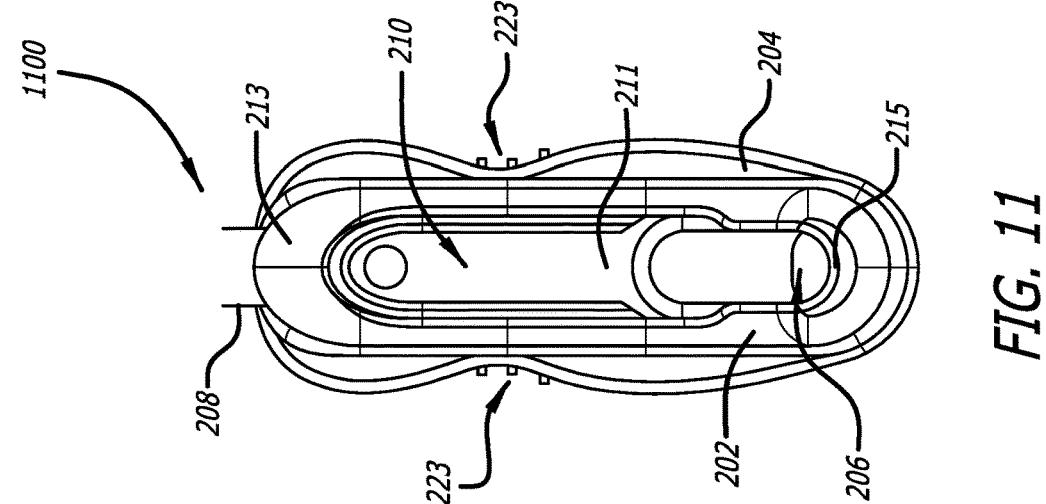
FIG. 11 illustrates a first view of a fourth FEC in accordance with some embodiments.
Figure 16:
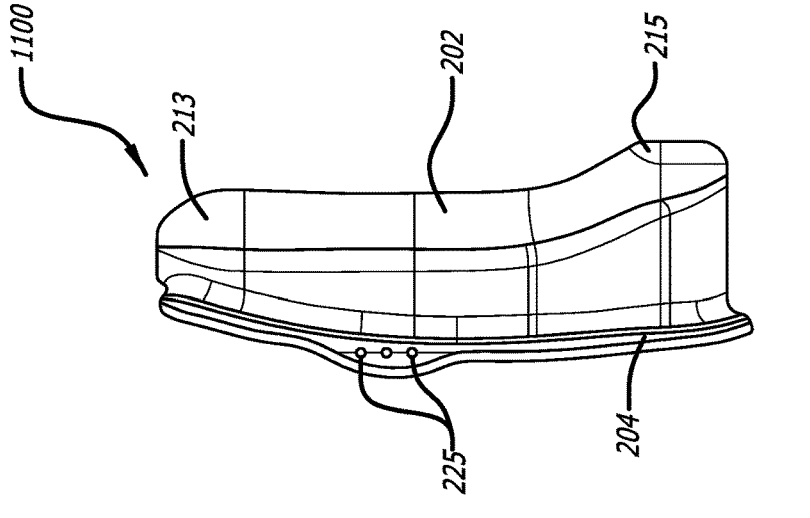
FIG. 16 illustrates a third, relatively large size for the fourth FEC in accordance with some embodiments.
Figure 15:
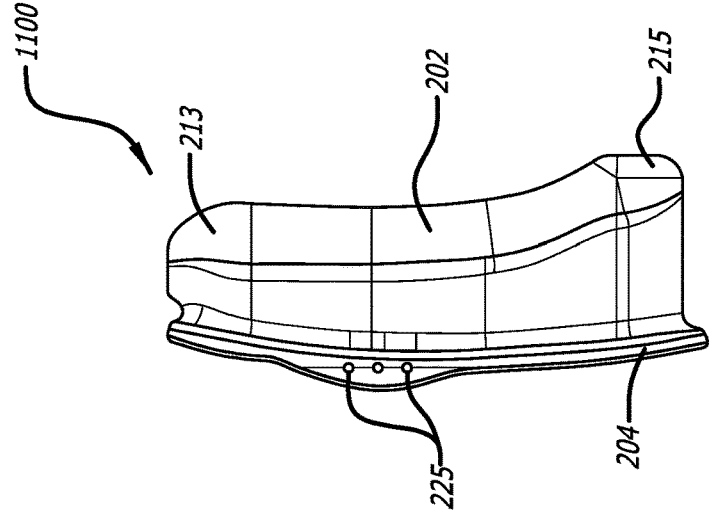
FIG. 15 illustrates a second, medium size for the fourth FEC in accordance with some embodiments.
Figure 14:
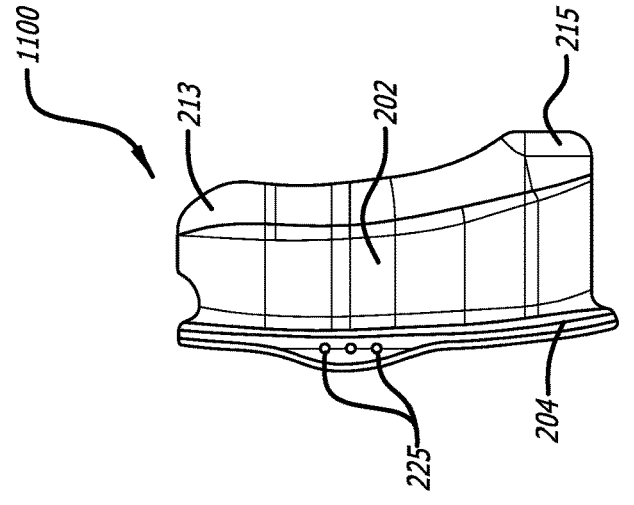
FIG. 14 illustrates a first, relatively small size for the fourth FEC in accordance with some embodiments.
Figure 17:
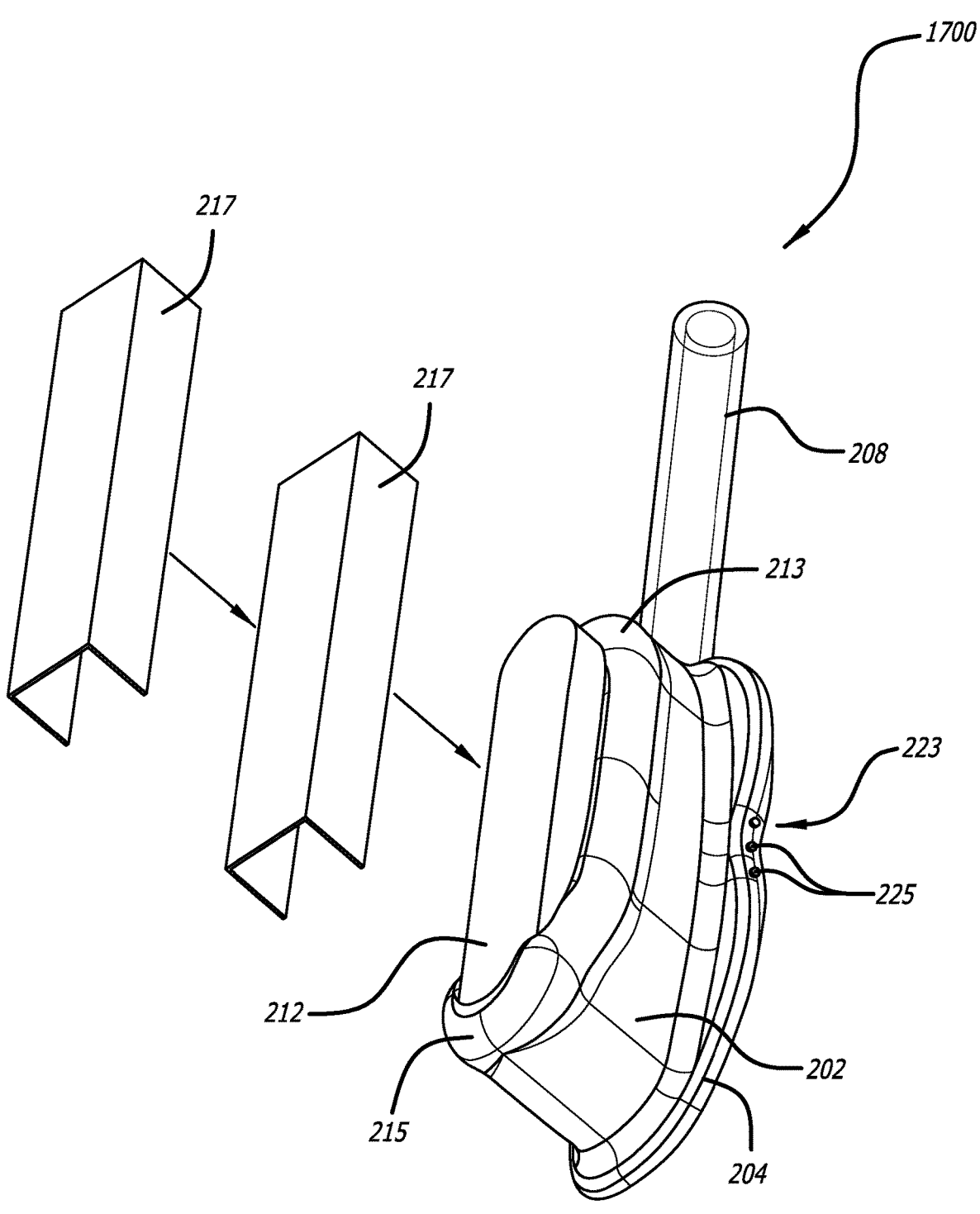
FIG. 17 illustrates a view of a fifth FEC in accordance with some embodiments.
Figures 18, 19:
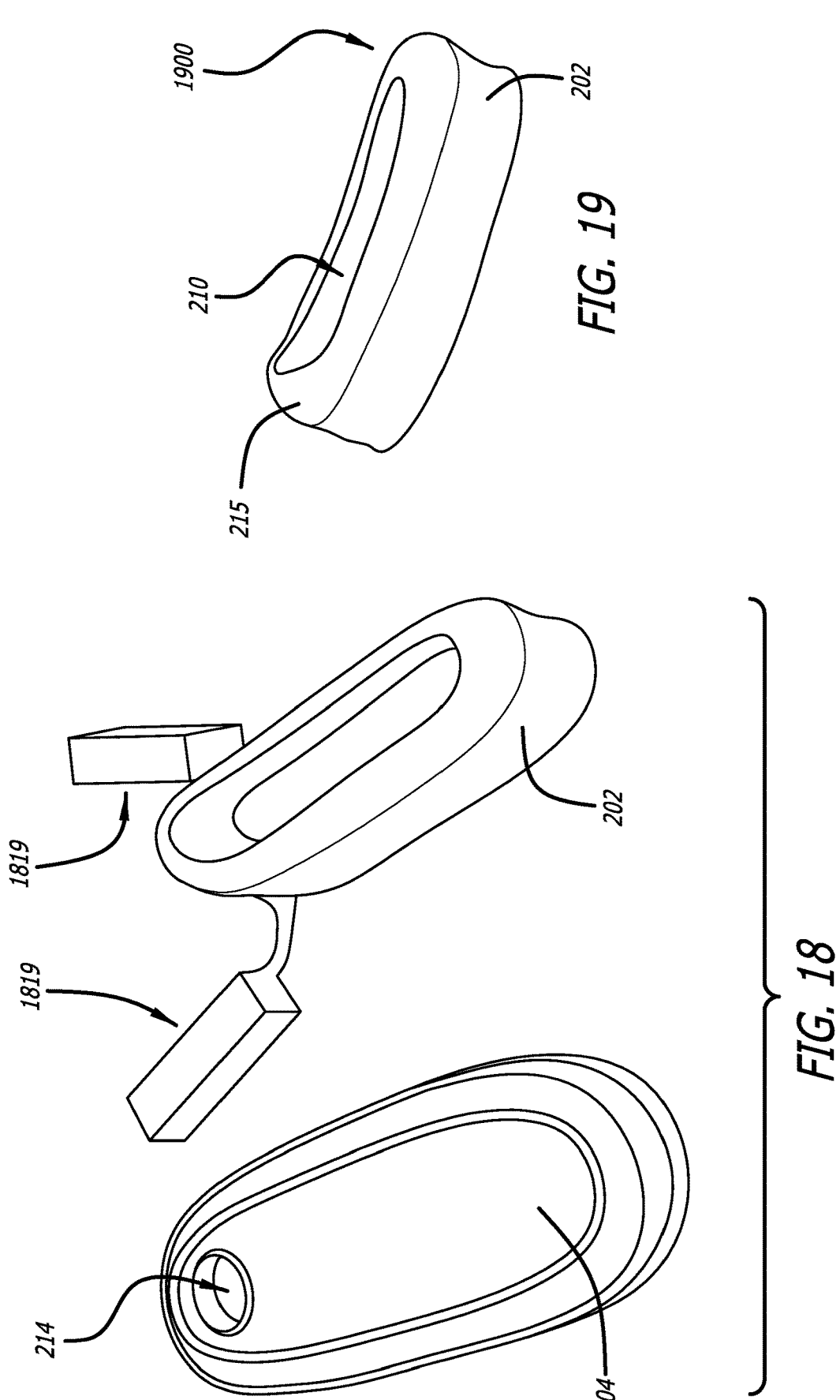
FIG. 18 illustrates a view of a sixth FEC in accordance with some embodiments.
FIG. 19 illustrates body and back pieces of the sixth FEC in accordance with some embodiments.

FIGS. 2 and 3 illustrate different views of a first FEC 200 in accordance with some embodiments. FIG. 5 illustrates a second FEC 500 in accordance with some embodiments. FIGS. 6-8 illustrate different views of a third FEC 600 in accordance with some embodiments. FIGS. 11-13 illustrate different views of a fourth FEC 1100 in accordance with some embodiments. FIG. 17 illustrates a view of a fifth FEC 1700 in accordance with some embodiments. FIG. 19 illustrates a view of a sixth FEC 1900 in accordance with some embodiments. For brevity, genus-type features among the FECs 200, 500, 600, 1100, 1700, and 1900 (e.g., the body 202, the back 204, and the connector 206) are referred to herein by a single reference number even though each FEC of the FECs 200, 500, 600, 1100, 1700, and 1900 might include species-type features that differentiate a particular genus-type feature from that of another FEC. For example, while the back 204 is a genus-type feature of each FEC of the FECs 200, 500, 600, 1100, 1700, and 1900, the back 204 of the FECs 500 and 600 includes a species-type feature in the pair of side notches 223 where the back 204 of the FECs 200 and 1900 does not. The back 204 of the FECs 500, 600, 1100, and 1700 is, therefore, different than the back 204 of the FECs 200 and 1900. That said, as set forth above, a particular embodiment disclosed herein can have features that can be readily separated from the particular embodiment and optionally combined with or substituted for features of any of a number of other embodiments disclosed herein.

As shown the FEC 200, 500, 600, 1100, 1700, or 1900 can include a body 202, a back 204, and a connector 206. In addition, the FEC 200, 500, 600, 1100, 1700, or 1900 can include catheter tubing 208.

The body 202 of the FEC 200, 500, 600, 1100, 1700, or 1900 can include a cavity 210 extending along a majority of a length of the body 202. The cavity 210 can, in turn, include a continuation of the connector hole 214 set forth below through a cavity bottom 211 of the cavity 210. The cavity 210 is configured to open toward a patient P like that of FIG. 1. Because the body 202 of at least the FEC 200 can be made of an open-cell foam as set forth below, the cavity 210 can include an impermeable coating over a surface of the cavity 210. The coating is configured to prevent urine from passing into or through the body 202, the back 204, or sides of at least the FEC 200 when made of the open-cell foam. For added impermeability, any combination of the body 202, the back 204, or the sides of at least the FEC 200 up to an entirety thereof can include the coating. Notably, FECs such as the FECs 500, 600, and 1900 need not include such a coating when thermoformed.

The body 202 of the FEC 200, 500, 600, 1100, 1700, or 1900 can include a contacting knoll 213 and a positioning knoll 215 opposite thereto extending from away from the body 202 in an opposite direction than the back 204. The positioning knoll 215 is configured to be aligned with a vaginal introitus when the FEC 200, 500, 600, 1100, 1700, or 1900 is tucked between inner labia (i.e., labia minora) for urine collection. Notably, the positioning knoll 215 of the FEC 600 or 1100 is truncated and, thusly, flatter than the positioning knoll 215 of the FEC 200, 500, or 1900. Advantageously, the positioning knoll 215 of the FEC 600 is less likely to enter the vaginal introitus in some patients than that of the FEC 200, 500, or 1900, thereby enhancing comfort to the patient P.

The FEC 200, 500, 600, 1100, 1700, or 1900 can further include an insert 212 of a porous medium such as an open-cell foam disposed in the cavity 210. The insert 212 is permeable and, therefore, configured to allow urine to pass therethrough for collection by the sump 220 set forth below. The open-cell foam can be the same as or different then the open-cell foam of, for example, the FEC 200. Notably, the insert 212 is compliant. Indeed, the insert 212 has a durometer and bulk modulus sufficient to provide comfort to the patient P for up to 8 or more hours without compressing to an extent that prevents the urine form passing through the insert 212. In addition, any FEC of the FECs 200, 500, 600, 1100, 1700, and 1900 including the insert 212 can also include one or more intake layers 217 disposed over the insert 212. The one-or-more intake layers 217 are configured to wick urine from its point of origin over the one-or-more intake layers 217, as needed, to increase throughput while a constant vacuum is maintained.

The back 204 of the FEC 200, 500, 600, 1100, 1700, or 1900 can include a connector hole 214 aligned with an end portion of the cavity 210. The connector hole 214 is configured to open away from the patient P such that the connector 206 disposed in the connector hole 214 faces away from the patient P.

Optionally, the back 204 of at least the FEC 200, 500, 600, or 1100 includes recesses (not shown) flanking the connector hole 214. When the connector 206 includes the pair of wings 222, the pair of wings 222 can be disposed in the pair of recesses. (See FIGS. 3 and 4 for the pair of wings 222 and the pair of wings 222 disposed in the pair of recesses.) The pair of wings 222 can be adhered to the pair of recesses, which increases a bonding interface and strengthens a bond between the back 204 of at least the FEC 200, 500, 600, or 1100 and the connector 206. That said, the back 204 of the FEC 200, 500, 600, or 1100 can alternatively be molded over the connector 206 with or without the pair of wings 222. Whether the connector 206 is adhered or overmolded, the back 204 of at least the FEC 200, 500, 600, or 1100 including the connector 206 can be flush.

The back 204 of at least the FEC 200, 500, 600, or 1100 can include a tubing channel 216. The tubing channel 216 extends along a length of the back 204 of the FEC 200, 500, 600, or 1100 from the connector hole 214 through an end of the back 204 opposite the connector hole 214. The back 204 of at least the FEC 600 or 1100 can include a depression 219 extending from each side of the tubing channel 216 along a length of the back 204 between the connector hole 214 and the end of the back 204 opposite the connector hole 214 such as between the connector hole 214 and the vent 221. The depression 219 is configured to facilitate pinching and folding at least the FEC 600 or 1100 lengthwise, which, in turn, facilitates positioning the FEC 600 or 1100 as set forth above for urine collection.

The back 204 of at least the FEC 500, 600, or 1100 can include a pair of side notches 223 evenly distributed in a pair of major sides of the back 204. Each side notch of the pair of side notches 223 is located in its corresponding major side of the back 204 between the connector hole 214 and the end of the back 204 opposite the connector hole 214 such as between the connector hole 214 and the vent 221. In addition, the pair of side notches 223 can be contoured with contoured finger surfaces, which finger surfaces, in turn, can be textured with ridges, bumps 225 as shown for the FEC 1100 in FIGS. 12 and 13, or, inversely, dimples. When the depression 219 is present such as that shown in FIG. 7 for the FEC 600 and FIG. 12 for the FEC 1100, the pair of side notches 223 flank the depression 219. With or without the depression 219, the pair of side notches 223 are configured to facilitate pinching at least the FEC 500, 600, or 1100, which, in turn, facilitates positioning the FEC 500, 600, or 1100 as set forth above for urine collection.

The back 204 of the FEC 200, 500, 600, 1100, 1700, or 1900 can include a stabilizer 218 extending from the back 204 in an opposite direction than that of the catheter tubing 208; however, the FECs 200, 500, are 600 are shown without such a stabilizer. When present, the stabilizer 218 can be integral with the back 204 of the FEC 200, 500, 600, 1100, 1700, or 1900 as shown in FIGS. 2 and 3 for the FEC 200 and FIG. 13 for the FEC 1100. Alternatively, the stabilizer 218 is removably coupled to the back 204 of the FEC 200, 500, 600, 1100, 1700, or 1900 for optional use by the patient P to stabilize the FEC 200, 500, 600, 1100, 1700, or 1900 by disposing the stabilizer 218 in an intergluteal cleft of the patient P.

The body 202 and the back 204 can be integral as shown in at least FIGS. 2, 5, 6, 11, and 17 for the FECs 200, 500, 600, 1100, and 1700. When integral, the body 202 and the back 204 can be a unitary molded (e.g., compression molded, injection molded, etc.) piece of a nonporous or porous thermoplastic such as an open- or closed-cell poly-urethane foam. When integral, the body 202 and the back 204 can alternatively be a unitary thermoformed (e.g., twin-sheet thermoformed) piece of a nonporous thermoplas-tic such as polyurethane or a thermoplastic elastomer ("TPE") such as thermoplastic polyurethane ("TPU"). Such a molded or thermoformed piece can have a durometer and bulk modulus sufficient to conform to the patient P under body pressure and provide comfort to the patient P for up to 8 or more hours. Alternatively, the body 202 and the back 204 can be separate pieces (e.g., two pieces) as shown in FIG. 19 for the FEC 1900. When separate pieces, each piece of the body 202 and the back 204 can be a thermoformed (e.g., single-sheet thermoformed) piece of nonporous ther-moplastic such as polyurethane for subsequently coupling together. Advantageously, removable grips 1819 configured to aid in positioning the FEC 1900 can be added to the body 202 of the FEC 1900 when thermoforming the body 202. Each piece of such thermoformed pieces can have a durom-eter and bulk modulus sufficient to provide comfort to the patient P for up to 8 or more hours.

The body 202 and the back 204 can include a vent 221 therebetween as shown in at least FIG. 5 for the FEC 500, FIGS. 7 and 8 for the FEC 600, and FIG. 12 for the FEC 1100. When present, the vent 221 can pass through the cavity bottom 211 and the back 204 in an end portion of the cavity 210 opposite that including the continuation of the connector hole 214. For enhancing comfort to the patient P, a shape of the vent 221 and its corresponding dimensions can be optimized to minimize a vacuum felt by the patient P while maintaining sufficient vacuum for urine collection. For example, the shape of the vent 221 of the FEC 600 approximates a half ellipse cut along a minor axis thereof in the view of the FEC 600 provided in FIG. 7. A base of the foregoing half ellipse can be increased to correspondingly increase air flow around the catheter tubing 208 and through the vent 221, thereby decreasing the vacuum felt by the patient P. Notably, removal of the cavity bottom 211 in the end portion of the cavity 210 for the vent 221 reduces structural integrity in the adjacent contacting knoll 213 opposite the positioning knoll 215. This softens the contact-ing knoll 213, which, in turn, enhances comfort for the patient P in that the contacting knoll 213 can come into contact with a portion of the female genitalia that can be sensitive to prolonged contact.

FIG. 4 illustrates the connector 206 of at least the FEC 200, 500, 600, 1100, or 1700 in accordance with some embodiments.

The connector 206 of at least the FEC 200, 500, 600, 1100, or 1700 can include a sump 220 configured to collect urine from the end portion of the cavity 210 for withdrawal from the FEC 200, 500, 600, 1100, or 1700.

Optionally, the connector 206 includes a pair of wings 222 extending from a back 224 of the connector 206. When the back 204 of at least the FEC 200, 500, 600, 1100, or 1700 includes the pair of recesses, the pair of wings 222 can be disposed in the pair of recesses. As set forth above, the pair of wings 222 can be adhered to the pair of recesses, which increases a bonding interface and strengthens a bond between the connector 206 and the back 204 of at least the FEC 200, 500, 600, 1100, or 1700. That said, the back 204 of at least the FEC 200, 500, 600, 1100, or 1700 can alternatively be molded over the connector 206 with or without the pair of wings 222. Whether the connector 206 is adhered or overmolded, the back 204 of at least the FEC 200, 500, 600, 1100, or 1700 including the connector 206 can be flush.

The connector 206 can be a molded (e.g., compression molded, injection molded, etc.) piece of a nonporous or porous thermoplastic. In an example, the connector 206 can be a molded piece of nonporous polyethylene. In another example, the connector 206 can be a molded piece of porous polyethylene such as an open- or closed-cell foam of poly-ethylene. The moldable polymer can be the same or different than that of the body 202 and the back 204 of the FEC 200, 500, 600, 1100, or 1700 whether the connector 206 is adhered to the back 204 or the back 204 is molded over the connector 206. While the connector 206 faces away from the patient P in at least the FEC 200, 500, 600, 1100, or 1700, its characteristics can transfer through a remainder of the FEC 200, 500, 600, 1100, or 1700 and affect patient comfort. As such, such a molded thermoplastic piece as the connector 206 can have a durometer and bulk modulus sufficient to provide comfort to the patient P for up to 8 or more hours.

Notably, the connector 206 can include an impermeable coating over a surface of at least the sump 220 if the connector 206 is a molded piece of porous thermoplastic, particularly the open-cell foam of polyethylene. Such a coating is configured to prevent urine from passing into or through the back 224 or sides of the connector 206 when the connector 206 is made of the foregoing open-cell foam of polyurethane. For added impermeability, up to an entirety of the connector 206 can include the coating.

The catheter tubing 208 can include a length disposed in the tubing channel 216 and an end portion disposed in the connector 206 as respectively shown in FIGS. 3 and 4. The catheter tubing 208 can be adhered to the tubing channel 216 and the connector 206; however, the length of the catheter tubing 208 disposed in the tubing channel 216 can be removably adhered to the tubing channel 216 such that the catheter tubing 208 can be pulled away from the tubing channel 216 if needed to provide comfort to the patient P. As shown, in FIG. 1, another end of the catheter tubing 208 can include a connector 226 configured to connect the FEC 200, 500, 600, 1100, 1700, or 1900 to the urine-drainage tubing 116.

Methods

Methods of the FECs 200, 500, 600, 1100, 1700, and 1900 include methods of using the foregoing FECs. For example, a method of using the FEC 200, 500, 600, 1100, 1700, or 1900 can include a connecting step, a disposing step, a switching step, and a urinating step.

The connecting step includes connecting the catheter tubing 208 of the FEC 200, 500, 600, 1100, 1700, or 1900 to the urine-drainage tubing 116 of a remainder of the urine-drainage system 100.

The disposing step includes disposing the insert 212 of the FEC 200, 500, 600, 1100, 1700, or 1900 over a urethral opening if the FEC 200, 500, 600, 1100, 1700, or 1900 is to include the insert 212. As set forth above, the insert 212 is disposed in the cavity 210 of the FEC 200, 500, 600, 1100, 1700, or 1900, which cavity includes the sump 220 in an end portion of the cavity 210.

Along with the disposing step, the method can include a stabilizing step. The stabilizing step includes disposing the stabilizer 218 of the FEC 200, 500, 600, 1100, 1700, or 1900 in an intergluteal cleft. As set forth above, if present, the stabilizer 218 extends from the back 204 of the FEC 200, 500, 600, 1100, 1700, or 1900 in an opposite direction than the catheter tubing 208.

The switching step includes switching on the pump 104 of the pump unit 102 of the urine-drainage system 100 to draw a vacuum through the insert 212.

The urinating step includes urinating into the FEC 200, 500, 600, 1100, 1700, or 1900 such that urine is drawn through the insert 212, into the sump 220, and out the catheter tubing 208 to the urine-drainage tubing 116.

The method can include another switching step. The other switching step includes switching off the pump 104 to stop drawing the vacuum.

The method can include an exchanging step. The exchanging step includes exchanging the FEC 200, 500, 600, 1100, 1700, or 1900 for a fresh FEC 200, 500, 600, 1100, 1700, or 1900 every 8 to 12 hours or as needed. With each exchanging step, the foregoing connecting step, disposing step, switching step, and urinating step can be repeated with the fresh FEC 200, 500, 600, 1100, 1700, or 1900.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A female external catheter ("FEC"), comprising:
   a catheter body including a cavity extending along a length of the catheter body, the cavity including an opening configured to open toward a patient;
   a fluid impermeable catheter back disposed opposite the opening of the cavity including a connector hole formed through the catheter back and aligned with an end portion of the cavity, the connector hole configured to open away from the patient; and
   a connector disposed in the connector hole, the connector including a sump configured to collect urine from the end portion of the cavity for withdrawal from the FEC.

2. The FEC of claim 1, wherein the catheter body and the catheter back are integral.

3. The FEC of claim 1, further comprising a stabilizer extending from the catheter back, the stabilizer configured for stabilizing the FEC on the patient using an intergluteal cleft of the patient.

4. The FEC of claim 3, wherein the stabilizer is integral with the catheter back.

5. The FEC of claim 1, wherein the catheter back includes a tubing channel extending along a length of the catheter back from the connector hole through an end of the catheter back opposite the connector hole.

6. The FEC of claim 5, further comprising catheter tubing disposed in the tubing channel, the catheter tubing including an end portion disposed in the connector.

7. The FEC of claim 1, wherein the connector includes a pair of wings extending from a connector back, the pair of wings disposed in a pair of recesses of the catheter back such that the catheter back and the connector back are flush.

8. The FEC of claim 1, wherein the catheter body and the catheter back are formed of an open-cell foam.

9. The FEC of claim 8, wherein the open-cell foam has a durometer and bulk modulus sufficient to provide comfort to the patient for up to 8 or more hours.

10. The FEC of claim 8, further comprising an impermeable cavity coating over a surface of the cavity, the impermeable cavity coating configured to prevent the urine from passing into the open-cell foam of the catheter body or the catheter back.

11. The FEC of claim 10, further including an open-cell foam insert disposed in the cavity, the open-cell foam insert configured to allow the urine to pass therethrough for collection by the sump.

12. The FEC of claim 11, wherein the open-cell foam insert has a durometer and bulk modulus sufficient to provide comfort to the patient for up to 8 or more hours without compressing to an extent that prevents the urine from passing through the open-cell foam insert.

13. The FEC of claim 11, further including one or more intake layers disposed over the open-cell foam insert.

14. The FEC of claim 1, wherein the catheter body and the catheter back are two thermoformed pieces of the FEC.

15. The FEC of claim 14, further comprising a removable stabilizer extending from the catheter back, the removable stabilizer configured for stabilizing the FEC on the patient using an intergluteal cleft of the patient.

16. The FEC of claim 14, further comprising catheter tubing including an end portion disposed in the connector.

17. The FEC of claim 14, further comprising an open-cell foam insert disposed in the cavity, the open-cell foam insert configured to allow the urine to pass therethrough for collection by the sump.

18. The FEC of claim 17, wherein the open-cell foam insert has a durometer and bulk modulus sufficient to provide comfort to the patient for up to 8 or more hours without compressing to an extent that prevents the urine from passing through the open-cell foam insert.

19. The FEC of claim 1, wherein the catheter body includes a positioning knoll over the end portion of the cavity, the positioning knoll configured to be aligned with a vaginal introitus when the FEC is tucked between inner labia.

20. The FEC of claim 1, further comprising a vent between the catheter body and the catheter back, the vent passing through a cavity bottom of the cavity and the catheter back in a second end portion of the FEC opposite that including the connector hole.

21. The FEC of claim 1, wherein the catheter back includes a depression along a length of the catheter back, the depression configured to facilitate pinching and folding the FEC lengthwise for positioning the FEC to collect the urine.

22. The FEC of claim 1, wherein the catheter back includes a pair of side notches evenly distributed in a pair of major sides of the back, the pair of side notches configured to facilitate pinching and folding the FEC lengthwise for positioning the FEC to collect the urine.

23. The FEC of claim 22, wherein the pair of side notches are contoured with contoured finger surfaces.

24. The FEC of claim 23, wherein the contoured finger surfaces are textured with ridges, bumps, or dimples.

\* \* \* \* \*